United States Patent [19]

Murase et al.

[11] Patent Number: 4,464,384
[45] Date of Patent: Aug. 7, 1984

[54] 2-PHENYLIMIDAZO[2,1-b]BENZO-THIAZOLE COMPOUNDS, SALTS THEREOF, PROCESS OF PRODUCING THEM, AND PHARMACEUTICAL COMPOSITIONS CONTAINING THEM

[75] Inventors: Kiyoshi Murase, Saitama; Toshiyasu Mase, Chiba; Hideki Arima, Tokyo; Kunihiro Niigata, Saitama; Kenichi Tomioka; Shinichiro Kobayashi, both of Saitama, all of Japan

[73] Assignee: Yamanouchi Pharmaceutical Co., Ltd., Tokyo, Japan

[21] Appl. No.: 449,759

[22] Filed: Dec. 14, 1982

[30] Foreign Application Priority Data

Dec. 23, 1981 [JP] Japan .................................. 56-208609
Oct. 27, 1982 [JP] Japan .................................. 57-188866

[51] Int. Cl.$^3$ .................. C07D 513/04; A61K 31/425
[52] U.S. Cl. .................................... 424/270; 548/151
[58] Field of Search ......................... 548/151; 424/270

[56] References Cited

FOREIGN PATENT DOCUMENTS 2056982 3/1981 United Kingdom ................ 548/151

Primary Examiner—Robert Gerstl
Attorney, Agent, or Firm—Burgess, Ryan & Wayne

[57] ABSTRACT

Novel 2-phenylimidazo[2,1-b]benzothiazole compounds shown by general formula I

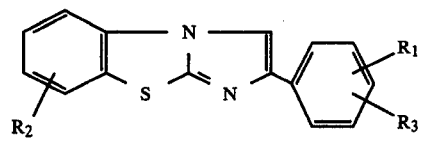

and the salts thereof, a process of producing the compounds, and pharmaceutical compositions containing the compounds.

The compounds of this invention act on immune response, in particular, suppress a delayed type hypersensitivity reaction, and are useful as antiallergic agents, antirheumatics, therapeutic agents for autoimmune diseases, and suppressants of rejection at tissue transplantation and skin graft.

9 Claims, No Drawings

2-PHENYLIMIDAZO[2,1-b]BENZOTHIAZOLE COMPOUNDS, SALTS THEREOF, PROCESS OF PRODUCING THEM, AND PHARMACEUTICAL COMPOSITIONS CONTAINING THEM

DETAILED DESCRIPTION OF THE INVENTION

This invention relates to novel 2-phenylimidazo[2,1-b]benzothiazole compounds, the salts thereof, a process of producing them, and pharmaceutical compositions containing these compounds.

More particularly, the invention relates to 2-phenylimidazo[2,1-b]benzothiazole compounds represented by the following general formula I

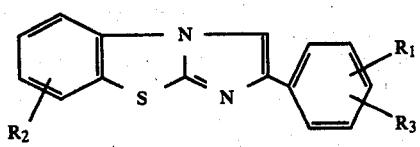

wherein one of $R_1$ and $R_2$ represents a group shown by the formula $-O-A-(B)_n-D$ (wherein A represents a carbonyl group or a sulfonyl group; B represents a saturated or unsaturated lower alkylene group which may be substituted by a carboxy group, an amino group, or a lower alkoxy group and may be interrupted by an oxygen atom; n represents 0 or 1; and D represents a carboxy group, a lower alkoxycarbonyl group, an amino group or a mono- or di-lower alkyl amino group or a phosphoric acid residue

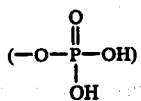

and the other of $R_1$ and $R_2$ represents a hydrogen atom; and $R_3$ represents a hydrogen atom, a halogen atom, or a lower alkoxy group, the salts thereof, a process of producing them, and pharmaceutical compositions containing these compounds.

In the definitions for foregoing general formula I, the term "lower" means a branched or straight carbon chain having 1-6 carbon atoms (in the unsaturated lower alkylene group, the carbon atom number is 2-6). Therefore, as a lower alkyl group, there are a methyl group, an ethyl group, a propyl group, an isopropyl group, a butyl group, an iso-butyl group, a sec-butyl group, a tert-butyl group, a pentyl group, an isoamyl group, a neopentyl group, etc., and as a lower alkoxy group, there are a methoxy group, an ethoxy group, an isopropoxy group, a butoxy group, etc. Also, as a saturated or unsaturated lower alkylene group, there are a methylene group, a methylmethylene group, an ethylene group, a trimethylene group, a propylene group, an ethylmethylene group, a tetramethylene group, a methyltrimethylene group, an ethylethylene group, a porpylmethylene group, an isopropylmethylene group, a dimethylethylene group, an ethylmethylmethylene group, a pentamethylene group, a methyltetramethylene group, an ethyltrimethylene group, a propylethylene group, a butylmethylene group, a dimethyltrimethylene group, an isopropylethylene group, an ethylmethylethylene group, a diethylmethylene group, a methylpropylmethylene group, a vinylene group, a methylvinylene group, a propenylene group, a butenylene group, a methylpropenylene group, an ethylvinylene group, a dimethylvinylene group, a pentenylene group, a methylbutenylene group, an ethylpropenylene group, a propylvinylene group, a dimethylpropenylene group, an ethylmethylvinylene group, etc. Furthermore, as a mono- or di-lower alkylamino group, there are a methylamino group, an ethylamino group, an isopropylamino group, a butylamino group, a dimethylamino group, a diethylamino group, a dipropylamino group, a di-t-butylamino group, an ethylmethylamino group, a methylpropylamino group, a butylethylamino group, etc. As a halogen atom, there are a chlorine atom, a bromine atom, etc.

The compounds of the foregoing general formula I provided by the present invention form acid addition salts or form salts with bases according to the kind of the substituents. This invention includes pharmaceutically acceptable salts of the compound of formula I and examples of such salts are the acid addition salts thereof with mineral acids such as hydrochloric acid, hydrobromic acid, nitric acid, sulfuric acid, etc., or organic acids such as methanesulfonic acid, p-toluenesulfonic acid, etc., and, as the salts thereof formed according to the kind of the substituents, the salts with alkali metals such as sodium, potassium, etc., the salts with alkaline earth metals such as calcium, etc., the ammonium salts, and the salts with organic bases such as methylamine, ethylamine, diethylamine, trimethylamine, triethylamine, pyridine, picoline, arginine, lysine, etc.

The compounds of this invention shown by general formula I act on immune response. For example, since these compounds suppress a delayed type hypersensitivity reaction which is a typical cell-mediated immunity, the compounds are useful as antiallergic agents, antirheumatics, therapeutic agents for autoimmune desease, and suppressants of rejection at tissue transplantation or skin graft. These compounds are particularly useful as delayed type hypersensitivity suppressants and antirheumatics. That is, hitherto, as antiallergic agents, in particular, as delayed type hypersensitivity suppressants, only steroids have been known. Antirheumatics are also in the same situation as above. However, when steroids are consecutively administered for a long period of time, serious side effects such as bone marrow depression occur and hence the development of non-steroidal antiallergic agents and antirheumatics has been desired. The compounds of this invention having a strong delayed type hypersensitivity suppressing activity can be used in place of these steroids or can reduce the amount of steroids by using together with steroids.

Also, since the compounds of this invention shown by formula I have very weak toxicity, the compounds can be used as medicaments for foregoing various uses.

The compounds of this invention shown by formula I are novel compounds obtained by acylating the hydroxyl group of the 2-phenylimidazo[2,1-b]benzothiazole derivatives previously provided by the inventors (U.S. patent application Ser. No. 176,907) with a carboxylic acid or sulfonic acid having a carboxy group, lower alkoxycarbonyl group, amino group, or dialkylamino group or phosphoric acid and a feature of the compounds is that the medical actions thereof such as delayed type hypersensitivity suppressing activity, etc., are more excellent than the aforesaid known hydroxy compounds. Another feature of the compounds of this invention is that the compounds are mostly water-soluble and have better oral absorption.

A medicament containing the compound of formula I of this invention as the main component is prepared in an ordinary manner using any desired carrier and excipient for preparation. The medicament may be administered orally as tablets, pills, capsules, granules, etc., or may be parenterally administered as injections, such as intravenous injection, intramuscular injection, etc., or as the form of aerosol, suppository, etc. The doses of the medicament are properly determined considering the symptons, age, sex, etc. of a patient, but the dose is usually 5-500 mg in case of oral adminstration and 2-300 mg in case of parenteral administration per day for an adult. The medicament is administered 2-3 times a day.

The compounds of this invention shown by general formula I are prepared by the following processes.

The compound of general formula I wherein one of $R_1$ and $R_2$ is the group shown by $-O-A-(B)_{\overline{n}}D$ and the other is a hydrogen atom can be prepared by reacting the compound shown by general formula II

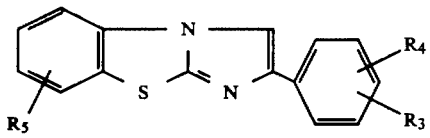

wherein one of $R_4$ and $R_5$ represents a hydroxy group and the other thereof represents a hydrogen atom and $R_3$ has the same significance as described above and the compound (carboxylic acid or sulfonic acid) shown by general formula III

III wherein A, B, D and n have the same significance as described above, or the reactive derivative thereof.

As the reactive derivative of the compound of formula III, there are acid halides such as acid chloride, acid bromide, etc.; acid azides; acid anhydrides; mixed acid anhydrides with an alkyl carbonate, an alkyl phosphorate, a dialkyl phosphite, sulfuric acid, etc.; acid amides with imidazole, etc.; and active esters such as p-nitrophenyl ester, 2,4-dinitrophenyl ester, etc.

It is preferred that the reaction is performed by reacting the compound of formula II and an equimolar amount or excessive molar amount of the compound of formula III or a reactive derivative thereof in an organic solvent under cooling, at room temperature, or heating. Examples of the organic solvent are acetone, tetrahydrofuran, dichloromethane, chloroform, pyridine, dimethylformamide, etc. In the case of using the compound of formula III in the free state, it is preferred to perform the reaction in the presence of a base such as pyridine, N,N'-dimethylaniline, etc., using a condensing agent such as N,N'-dicyclohexylcarbodiimide, N,N'-carbonylimidazole, etc. In this case, N-hydroxybenztriazole may be used together with the condensing agent.

When in the compound of formula III, B or D has a free amino group or carboxy group, it is preferred that the compound is used by previously protecting the amino group or carboxy group. As the proper protective group for the amino group, there are a formyl group, t-butoxycarbonyl group, a benzyloxycarbonyl group, etc., and as the protective group for a carboxy group, there are a t-butyl group, a benzhydryl group, a p-methoxybenzyl group, a p-nitrobenzyl group, etc. The protective group can be removed from the reaction product by an ordinary manner such as a treatment under an acidic condition or a catalytic reduction.

Also, in the foregoing compounds, the compound having a lower alkoxycarbonyl group as the terminal substituent D at the side chain can be produced by reacting the compound having a carboxy group as the terminal substituent D in the foregoing compounds or a reactive derivative thereof with a lower alcohol. This reaction can be performed according to the foregoing reaction of the compound of formula II and the compound of formula III.

Furthermore, the compound of formula I wherein one of $R_1$ and $R_2$ is a phosphoric acid residue and the other is a hydrogen atom can be produced by reacting the compound of formula II and a reactive derivative of phosphoric acid such as, for example, phosphorus oxychloride. It is preferred to perform the reaction in an organic solvent under cooling.

The product thus formed can be isolated and purified by an ordinary manner such as filtration, extraction, recrystallization, column chromatography, etc.

Then, the excellent pharmaceutical actions of the compounds of this invention will be shown by the following experiments.

Delayed-type hypersensitivity reaction induced by picryl chloride in mice:

Male ICR mice 7 weeks old were sensitized by applying 0.1 ml of 7% picryl chloride solution in acetone to the shaved abdomen.[1] After a 7-day sensitization period, the mice were challenged by painting the inside of each ear with 0.02 ml of 1% picryl chloride solution in olive oil. The ear thickness was measured with a dial thickness gauge before and 24 hr after the challenge and the differences were obtained. Drug actions in the sensitization phase were examined by administering the drug from day 0 to day 2 after immunization.
[1] Asherson, G. L. and Ptak, W. Immunology 15, 405 (1968)

As shown in Table I, 2-(m-Carboxyacetoxyphenyl)imidazo[2,1-b]benzothiazole at 6.3-100 mg/kg p.o. suppressed the delayed-type hypersensitivity (DTH) response. Other compounds of this invention also suppressed the DTH response.

TABLE I

Effects of the compounds of this invention and known medicaments on picryl chloride-induced delayed-type hypersensitivity response in mice.

| Drug | Dose (mg/kg) | N | Ear thickness increment (1/100 mm) | Inhibition (%) |
|---|---|---|---|---|
| Known compounds | | | | |
| 2-(m-Hydroxyphenyl)- | 25 | 8 | 5.3 ± 0.8 | 14.5 |
| imidazo[2,1-b]benzo- | 50 | 8 | 3.9 ± 0.5* | 37.1 |
| thiazole | 100 | 8 | 2.4 ± 0.6** | 61.3 |
|  | 200 | 8 | 2.8 ± 0.9* | 54.8 |
|  | 400 | 8 | 1.3 ± 0.6** | 79.0 |
| control | — | 10 | 6.2 ± 0.8 | — |
| Prednisolone | 6.3 | 5 | 6.1 ± 1.1 | 31.5 |
|  | 50 | 5 | 4.5 ± 1.1* | 49.4 |
| control | — | 10 | 8.9 ± 1.2 | — |
| Cyclophosphamide | 50 | 5 | 1.2 ± 0.7* | 62.5 |
| control | — | 10 | 3.2 ± 0.4 | — |
| Compounds of this invention | | | | |
| 2-(m-Carboxyacetoxy- | 3.1 | 9 | 4.8 ± 0.4 | 21.3 |
| phenyl)-imidazo[2,1-b]- | 6.3 | 9 | 4.2 ± 0.5* | 31.1 |
| benzothiazole | 12.5 | 8 | 2.6 ± 0.8** | 57.4 |
| Ex. 1) | 25 | 8 | 3.1 ± 0.9* | 49.2 |

TABLE I-continued

Effects of the compounds of this invention and known medicaments on picryl chloride-induced delayed-type hypersensitivity response in mice.

| Drug | Dose (mg/kg) | N | Ear thickness increment (1/100 mm) | Inhibition (%) |
|---|---|---|---|---|
|  | 50 | 8 | 1.8 ± 0.6** | 70.5 |
|  | 100 | 8 | 2.3 ± 0.6** | 62.2 |
| control | — | 10 | 6.1 ± 0.7 | — |
| 2-(m-cis-3-Carboxy- | 12.5 | 7 | 4.6 ± 1.1 | 25.8 |
| propenoyloxyphenyl)- | 25 | 7 | 3.1 ± 0.8* | 50.0 |
| imidazo[2,1-b]- | 50 | 7 | 2.6 ± 0.8* | 58.1 |
| benzothiazole | 100 | 7 | 1.9 ± 0.5** | 69.4 |
| hydrochloride (Ex. 6) | 200 | 7 | 1.9 ± 0.5** | 69.4 |
| control | — | 10 | 6.2 ± 0.8 | — |
| 2-(m-trans-3-Carboxy- | 12.5 | 8 | 3.3 ± 0.4** | 46.8 |
| propenoyloxyphenyl)- | 25 | 8 | 2.9 ± 0.7* | 53.2 |
| imidazo[2,1-b]- | 50 | 8 | 1.9 ± 0.5** | 69.4 |
| benzothiazole | 100 | 7 | 1.6 ± 0.3** | 74.2 |
| (Ex. 7,b) | 200 | 7 | 1.1 ± 0.7** | 82.2 |
| control | — | 10 | 6.2 ± 0.8 | — |
| 2-(m-trans-3-Carboxy- | 6.3 | 6 | 5.9 ± 0.9 | 32.0 |
| propenoyloxyphenyl)- | 12.5 | 6 | 2.8 ± 1.0** | 68.2 |
| imidazo[2,1-b]- | 25 | 6 | 2.8 ± 1.3** | 68.2 |
| benzothiazole | 50 | 6 | 2.9 ± 1.0** | 67.0 |
| hydrochloride | 100 | 6 | 2.8 ± 0.7** | 68.2 |
| (Ex. 7,a) | 200 | 6 | 1.9 ± 0.7** | 88.6 |
| control | — | 11 | 8.8 ± 1.1 | — |
| 2-[m-(2-Carboxy- | 25 | 5 | 4.7 ± 0.4* | 21.7 |
| propionyloxy)phenyl]- | 200 | 5 | 3.2 ± 1.0** | 46.7 |
| imidazo[2,1-b] benzo- |  |  |  |  |
| thiazole hydrochloride |  |  |  |  |
| (EX. 9) |  |  |  |  |
| control | — | 10 | 6.0 ± 0.4 | — |
| 2-(m-γ-Glutamyloxy- | 25 | 5 | 3.9 ± 0.6** | 35.0 |
| phenyl)imidazo[2,1-b]- | 200 | 5 | 3.0 ± 0.7** | 50.0 |
| benzothiazole hydrate |  |  |  |  |
| hydrochloride (Ex. 10) |  |  |  |  |
| control | — | 10 | 6.0 ± 0.4 | — |
| 2-[m-(N,N—Dimethyl- | 25 | 5 | 4.4 ± 0.5** | 42.1 |
| aminoacetoxy)phenyl]- | 200 | 5 | 4.0 ± 1.3* | 47.4 |
| imidazo[2,1-b]- |  |  |  |  |
| benzothiazole |  |  |  |  |
| hydrochloride (Ex. 11) |  |  |  |  |
| control | — | 10 | 7.6 ± 0.7 | — |
| 2-(m-α-Aspartyloxy- | 25 | 5 | 3.5 ± 0.4** | 41.0 |
| phenyl)imidazo[2,1-b]- | 200 | 5 | 3.3 ± 0.7** | 45.0 |
| benzothiazole |  |  |  |  |
| di-hydrobromide | (Ex. 15) |  |  |  |
| control | — | 10 | 6.0 ± 0.4 | — |
| 2-[m-(trans-3-Ethoxy- | 12.5 | 6 | 4.6 ± 1.6* | 47.7 |
| carboxylpropenoyloxy)- | 25 | 6 | 3.2 ± 0.3** | 63.6 |
| phenyl]imidazo[2,1-b]- | 50 | 6 | 3.3 ± 1.1** | 62.5 |
| benzothiazole (Ex. 27) | 100 | 6 | 1.1 ± 0.6** | 87.6 |
|  | 200 | 6 | 3.5 ± 0.9** | 60.2 |
| control | — | 11 | 8.8 ± 1.1 | — |
| 2-[m-(cis-3-Ethoxy- | 25 | 6 | 4.8 ± 0.9* | 45.5 |
| carbonylpropenoyloxy)- | 50 | 6 | 1.6 ± 0.5** | 81.8 |
| phenyl]imidazo[2,1-b]- | 100 | 6 | 3.7 ± 0.7** | 58.0 |
| benzothiazole (Ex. 24) | 200 | 6 | 1.3 ± 0.4** | 85.2 |
| control | — | 11 | 8.8 ± 1.1 | — |
| 2-[m-(3-Ethoxy- | 25 | 7 | 4.5 ± 0.9* | 47.1 |
| carbonylpropionyloxy)- | 50 | 7 | 4.4 ± 1.1* | 48.2 |
| phenyl]imidazo[2,1-b]- | 100 | 7 | 3.4 ± 1.1* | 60.0 |
| benzothiazole (Ex. 22) | 200 | 7 | 3.0 ± 0.3** | 64.7 |
| control | — | 10 | 8.5 ± 1.2 | — |

*p < 0.05
**P < 0.01: Significantly differed from the control value.

Then, the invention will further be explained in detail by the following examples.

EXAMPLE 1

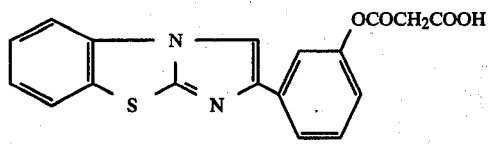

To a mixture of 2.7 g of 2-(m-hydroxyphenyl-)imidazo[2,1-b]benzothiazole, 1.6 g of potassium fluoride, and 100 ml of dimethylformamide was added a solution of 1.5 g of malonic acid monochloride in 10 ml of tetrahydrofuran at room temperature and the mixture was stirred for one hour at room temperature. The reaction mixture thus obtained was concentrated under reduced pressure and the residue was dissolved in 200 ml of ethyl acetate. The ethyl acetate solution was washed with water and extracted several times with 5% aqueous solution of sodium hydrogencarbonate. After washing the extract with ethyl acetate, the extract was acidified by the addition of concentrated hydrochloric acid, and then extracted thrice each time with 50 ml of ethyl acetate. The extract was washed with water, dried over anhydrous magnesium sulfate, and concentrated under reduced pressure to about 60 ml. By allowing to stand the residue thus formed overnight, 1.73 g of 2-(m-carboxyacetoxyphenyl)imidazo[2,1-b]benzothiazole was obtained.

Melting point: 159°–161° C.

Elemental analysis for $C_{18}H_{12}N_2O_4S$:

|  | C (%) | H (%) | N (%) | S (%) |
|---|---|---|---|---|
| Calculated: | 61.36 | 3.43 | 7.95 | 9.10 |
| Found: | 61.43 | 3.50 | 7.86 | 8.90 |

EXAMPLE 2

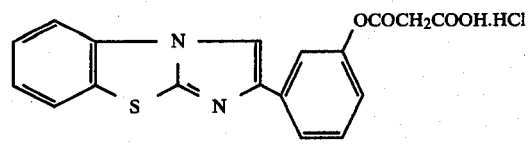

(a) In 20 ml of anhydrous pyridine were dissolved 1.3 g of 2-(m-hydroxyphenyl)imidazo[2,1-b]benzothiazole, 1.68 g of malonic acid mono-p-methoxybenzyl ester, and 1.56 g of dicyclohexylcarbodiimide and then the solution was stirred for 2 hours at room temperature. After the reaction was over, pyridine was distilled off and 100 ml of ethyl acetate was added to the residue thus formed. After filtering off undissolved dicyclohexyl urea, the ethyl acetate solution was washed in succession with 30 ml each of an aqueous solution of sodium hydrogen carbonate, a satruated aqueous solution of sodium chloride, 1N hydrochloric acid, and a saturated aqueous solution of sodium chloride, and after drying the solution over anhydrous magnesium sulfate, ethyl acetate was distilled off under reduced pressure. The crystals thus formed were recrystallized from 20 ml of toluene to provide 2.13 g of white crystals of 2-[m-(p-methoxyphenylmethoxycarbonylacetoxy)phenyl-]imidazo[2,1-b]benzothiazole.

Melting point: 120°–122° C.

Elemental analysis for $C_{26}H_{20}N_2O_5S$:

|  | C (%) | H (%) | N (%) | S (%) |
|---|---|---|---|---|
| Calculated: | 66.09 | 4.27 | 5.93 | 6.78 |
| Found: | 66.23 | 4.22 | 5.87 | 6.89 |

(b) In 5 ml of anhydrous dichloromethane was dissolved 1.146 g of 2-[m-(p-methoxyphenylmethoxycarbonylacetoxy)phenyl]imidazo[2,1-b]benzothiazole and after adding thereto 0.4 ml of anisole, the mixture was cooled with ice-water. Then, 5 ml of trifluoroacetic acid was added dropwise to the mixture and the resultant mixture was stirred for one hour. The reaction mixture thus formed was concentrated under reduced pressure and the oily product thus obtained was dissolved in 10 ml of anhydrous tetrahydrofuran. Then, while stirring the mixture under ice-cooling, 2 ml of 2N hydrogen chloride ethanol solution was added to the solution and white crystals thus precipitated were recovered by filtration to provide 911 mg of 2-(m-carboxyacetoxyphenyl)imidazo[2,1-b]benzothiazole hydrochloride.

Melting point: above 165° C. (decomd.).
Elemental analysis for $C_{18}H_{13}N_2O_4SCl$:

|  | C (%) | H (%) | N (%) | S (%) | Cl (%) |
|---|---|---|---|---|---|
| Calculated: | 55.60 | 3.37 | 7.20 | 8.25 | 9.12 |
| Found: | 55.47 | 3.46 | 7.13 | 8.04 | 9.17 |

EXAMPLE 3

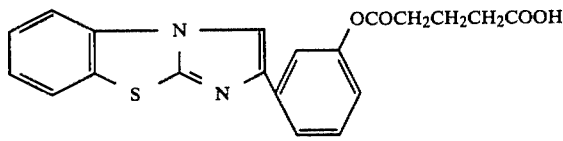

In 25 ml of pyridine were dissolved 8 g of 2-(m-hydroxyphenyl)imidazo[2,1-b]benzothiazole and 10 g of glutaric anhydride and after heating the solution at 100°-110° C. for 30 minutes, the solution was concentrated under reduced pressure. To the residue thus formed was added 200 ml of 5% cooled aqueous acetic acid and the reaction product was extracted with 200 ml of ethyl acetate. The extract was washed with water and quickly dried over anhydrous magnesium sulfate, and then the extract was concentrated under reduced pressure to about 70 ml. Then, the crystals thus precipitated were recovered by filtration and dried to provide 8.8 g of 2-[m-(4-carboxybutyryloxy)phenyl]imidazo[2,1-b]benzothiazole.

Melting point: 168°-171° C.
Elemental analysis for $C_{20}H_{16}N_2O_4S$:

|  | C (%) | H (%) | N (%) | S (%) |
|---|---|---|---|---|
| Calculated: | 63.15 | 4.24 | 7.36 | 8.43 |
| Found: | 63.45 | 4.32 | 7.64 | 8.46 |

By following the same procedure as in Example 3 using other corresponding starting compounds, the compounds shown in Examples 4 and 5 were obtained.

EXAMPLE 4

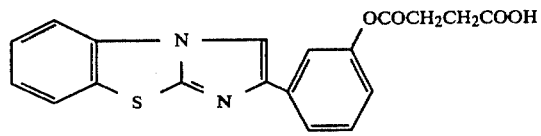

2-[m-(3-Carboxypropionyloxy)phenyl]imidazo[2,1-b]benzothiazole.
Melting point: 138°-139° C.
Elemental analysis for $C_{19}H_{14}N_2O_4S$:

|  | C (%) | H (%) | N (%) | S (%) |
|---|---|---|---|---|
| Calculated: | 62.29 | 3.85 | 7.65 | 8.75 |
| Found: | 62.02 | 3.92 | 7.42 | 8.40 |

EXAMPLE 5

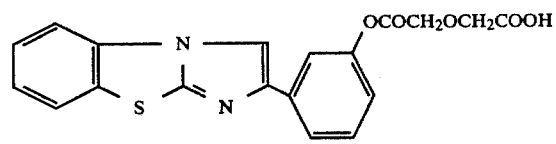

m-(2-Imidazo[2,1-b]benzothiazolyl)phenoxycarbonylmethoxy acetic acid.
Melting point: 185°-190° C.
Elemental analysis for $C_{19}H_{14}N_2O_5S$:

|  | C (%) | H (%) | N (%) |
|---|---|---|---|
| Calculated | 59.68 | 3.69 | 7.33 |
| Found: | 59.64 | 3.82 | 7.29 |

EXAMPLE 6

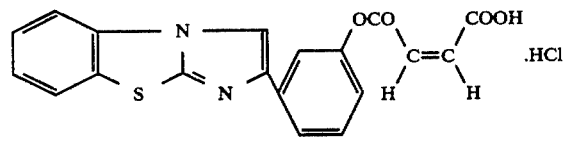

(a) In 100 ml of tetrahydrofuran were dissolved 7.5 g of maleic acid mono-p-methoxybenzyl ester obtained by reacting maleic anhydride and p-methoxybenzyl alcohol and 4.2 g of N-hydroxybenztriazole and after ice-cooling the solution to 3°-5° C., 7 g of dicyclohexylcarbodiimide was added to the solution followed by stirring for 15 minutes. To the reaction mixture was added 6 g of 2-(m-hydroxyphenyl)imidazo[2,1-b]benzothiazole and after stirring the mixture for 3 hours at room temperature, the reaction mixture was further stirred for 15 minutes at 50°-60° C. After cooling, urea thus precipitated was filtered off, and the filtrate was concentrated under reduced pressure. The residue was dissolved in 100 ml of ethyl acetate, the solution was washed twice each time with 30 ml of a saturated aqueous solution of sodium hydrogen-carbonate and after drying the solution over anhydrous magnesium sulfate, the solvent was distilled off under reduced pressure. The residue was applied to silical gel column chromatography and eluated with a mixture of benzene and ethyl acetate (95:5) to provide 6.5 g of 2-(m-cis-3-p-methoxyphenylmethoxycarbonylpropenoyloxyphenyl)imidazo[2,1-b]benzothiazole.

Melting point: 143°-145° C.
Elemental analysis for $C_{27}H_{20}N_2O_5S$:

|  | C (%) | H (%) | N (%) | S (%) |
|---|---|---|---|---|
| Calculated: | 66.93 | 4.16 | 5.78 | 6.62 |
| Found: | 67.21 | 4.09 | 5.60 | 6.41 |

(b) To an ice-cooled mixture of 20 ml of trifluoroacetic acid and 3 ml of anisole was added 5.3 g of the product in foregoing step (a) and after stirring the mixture for 30 minutes at room temperature, the mixture was concentrated under reduced pressure. To the residue were added 20 ml of 2N hydrogen chloride ethanol solution and 50 ml of ether, the crystals thus precipitated were recovered by filtration and dried to provide 3.8 g of 2-(m-cis-3-carboxypropenoyloxyphenyl)imidazo[2,1-b]benzothiazole hydrochloride.

Melting point: 250°-253° C.
Elemental analysis for $C_{19}H_{13}N_2O_4SCl$:

|  | C (%) | H (%) | N (%) | S (%) | Cl (%) |
|---|---|---|---|---|---|
| Calculated: | 56.93 | 3.27 | 6.99 | 8.00 | 8.84 |
| Found: | 56.92 | 3.12 | 7.05 | 7.71 | 8.54 |

EXAMPLE 7

(a)

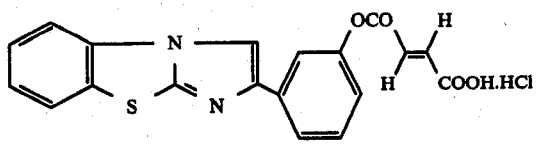

In 30 ml of pyridine were dissolved 3.9 g of fumaric acid mono-p-methoxybenzyl ester and 3.3 g of 2-(m-hydroxyphenyl)imidazo[2,1-b]benzothiazole and after adding thereto 0.5 ml of 4N hydrogen chloride dioxane solution, 3.4 g of dicyclohexylcarbodiimide was added to the mixture at 15°-20° C. After stirring the reaction mixture for 3 hours at 20°-25° C., urea thus precipitated was filtered off, and the filtrate was concentrated under reduced pressure. The residue thus formed was dissolved in 50 ml of methylene chloride, the solution was washed twice each time with 40 ml of water, dried over anhydrous magnesium sulfate, and then concentrated under reduced pressure. The residual solids were recrystallized from toluene to provide 5.5 g of 2-(m-trans-3-p-methoxyphenylmethoxycarbonylpropenoyloxyphenyl)imidazo[2,1-b]benzothiazole.

Melting point: 144°-146° C.
Elemental analysis for $C_{27}H_{20}N_2O_5S$:

|  | C (%) | H (%) | N (%) | S (%) |
|---|---|---|---|---|
| Calculated: | 66.93 | 4.16 | 5.78 | 6.62 |
| Found: | 66.63 | 4.15 | 5.74 | 6.47 |

In a mixture of 15 ml of methylene chloride and 7.5 ml of formic acid was dissolved 5 g of the foregoing product and when a hydrogen chloride gas was introduced into the mixture at 6°-14° C., white crystals began to crystallize after about 8 minutes. To the reaction mixture was added 30 ml of methylene chloride and after stirring the mixture for 10 minutes, 100 ml of ethyl acetate was added to the mixture followed by stirring for 10 minutes. Crystals thus formed were collected, washed with ethyl acetate and dried to provide 4.1 g of 2-(m-trans-3-carboxypropenoyloxyphenyl)imidazo[2,1-b]benzothiazole hydrochloride.

Decomposition point: 240°-243° C.

(b) To a mixture of 40 ml of tetrahydrofuran and 5 ml of water were added 3.7 g of the product obtained in foregoing step (a) and 0.8 g of sodium acetate, after stirring the mixture for about 10 minutes at 50°-60° C., 30 ml of water was added to the mixture and then tetrahydrofuran was distilled off under reduced pressure. The crystals thus formed were recovered by filtration, washed with water, and dried to provide 3.1 g of 2-(m-trans-3-carboxypropenoyloxyphenyl)imidazo[2,1-b]benzothiazole.

Decomposition point: 252° C.
Elemental analysis for $C_{19}H_{12}N_2O_4S$:

|  | C (%) | H (%) | N (%) | S (%) |
|---|---|---|---|---|
| Calculated: | 62.63 | 3.32 | 7.69 | 8.80 |
| Found: | 62.59 | 3.10 | 7.68 | 8.65 |

EXAMPLE 8

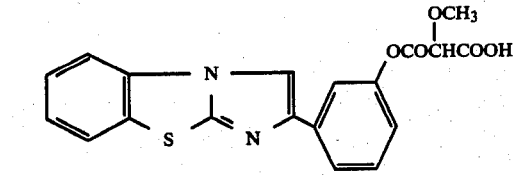

By following the same procedure as in Example 6 using 3.7 g of methoxymalonic acid mono-tert-butyl ester and 5 g of 2-(m-hydroxyphenyl)imidazo[2,1-b]benzothiazole, 6 g of 2-[m-(α-carboxy-α-methoxyacetoxy)phenyl]imidazo[2,1-b]benzothiazole.hydrochloride was obtained through 2-[m-(α-tert-butoxycarbonyl-α-methoxyacetoxy)phenyl]imidazo[2,1-b]benzothiazole (yield 7.3 g). Then, to 3 g of the hydrochloride were added a small amount of pyridine and 50 ml of ethyl acetate to dissolve the hydrochloride and 10% acetic acid was added to the solution, thereby crystals precipitated. The crystals thus formed were recovered by filtration, washed with isopropanol, and dried to provide 2.1 g of 2-[m-(α-carboxy-α-methoxyacetoxy)phenyl]imidazo[2,1-b]benzothiazole.

Melting point: 110°-113° C.
Elemental analysis for $C_{19}H_{14}N_2O_5S$:

|  | C (%) | H (%) | N (%) | S (%) |
|---|---|---|---|---|
| Calculated: | 59.68 | 3.69 | 7.33 | 8.38 |
| Found: | 59.44 | 3.79 | 7.22 | 8.43 |

EXAMPLE 9

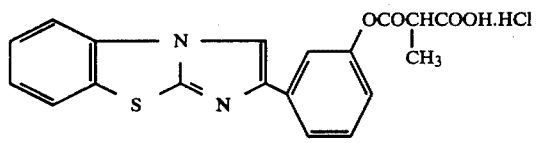

By following the same procedure as in Example 2 using 7.3 g of 2-(m-hydroxyphenyl)imidazo[2,1-b]benzothiazole and methylmalonic acid mono-tert-butyl ester, 7.26 g of 2-[m-(2-carboxypropionyloxy)phenyl]imidazo[2,1-b]benzothiazole.hydrochloride was obtained through 2-[m-(2-tert-butoxycarbonylpropionyloxy)phenyl]imidazo[2,1-b]benzothiazole (yield 10.1 g).

Melting point: 143°–146° C. (decomd.).
Elemental analysis for $C_{19}H_{15}N_2O_4ClS$:

|  | C (%) | H (%) | N (%) | S (%) | Cl (%) |
|---|---|---|---|---|---|
| Calculated: | 56.65 | 3.75 | 6.95 | 7.96 | 8.80 |
| Found: | 56.72 | 3.66 | 6.89 | 7.98 | 8.62 |

EXAMPLE 10

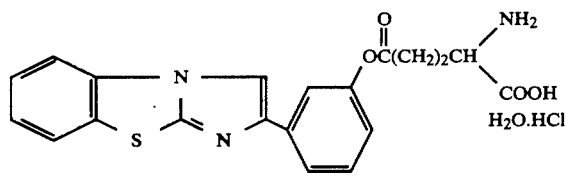

By following the same procedure as in Example 2 using 5 g of 2-(m-hydroxyphenyl)imidazo[2,1-b]benzothiazole and 4 g of N-tert-butoxycarbonylglutamic acid α-tert-butyl ester, 4.8 g of 2-[m-(4-tert-butoxycarbonyl-4-tert-butoxycarbonylaminobutyryloxy)phenyl]imidazo[2,1-b]benzothiazole was obtained. By treating 3 g of the compound as in Example 2, 2.1 g of 2-[m-γ-glutamyloxyphenyl]imidazo[2,1-b]benzothiazole hydrochloride monohydrate was obtained.

Melting point: 144°–146° C.
Elemental analysis for $C_{20}H_{20}N_3O_5ClS$:

|  | S (%) | Cl (%) |
|---|---|---|
| Calculated: | 7.13 | 7.88 |
| Found: | 6.86 | 8.03 |

EXAMPLE 11

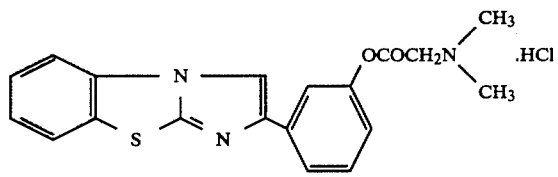

To 100 ml of pyridine were added 2.6 g of 2-(m-hydroxyphenyl)imidazo[2,1-b]benzothiazole and 1.5 g of dimethylglycine hydrochloride and after cooling the mixture to 3°–5° C., 2.1 g of dicyclohexylcarbodiimide was added to the mixture. After stirring the mixture overnight, urea thus precipitated was filtered off and the filtrate was concentrated under reduced pressure. To the residue was added 30 ml of water, insoluble matters were filtered off, and the filtrate was satruated by sodium chloride and extracted twice each time with 30 ml of n-butanol. To the extract was added 3 g of anhydrous magnesium sulfate, after shaking the mixture, the mixture was filtered, and the filtrate was concentrated under reduced pressure. While solids thus formed were washed successively with isopropanol and ethyl acetate, and dried to provide 1.6 g of 2-[m-(N,N-dimethylaminoacetoxy)phenyl]imidazo[2,1-b]benzothiazole hydrochloride.

Melting point: 210°–212° C.
Elemental analysis for $C_{19}H_{18}N_3O_2SCl$:

|  | C (%) | H (%) | N (%) | Cl (%) |
|---|---|---|---|---|
| Calculated: | 58.83 | 4.68 | 10.83 | 9.14 |
| Found: | 58.73 | 4.69 | 10.66 | 9.24 |

EXAMPLE 12

(a) In a mixture of 30 ml of pyridine and 30 ml of tetrahydrofuran were dissolved 5.25 g of N-tert-butoxycarbonylglycine and 4.2 g of N-hydroxybenzotriazole and after adding thereto 6.3 g of dicyclohexylcarbodiimide under cooling, the mixture was stirred for one hour at 5°–10° C. and then for 2 hours at room temperature. Then, urea thus formed was filtered off and after adding 6 g of 2-(m-hydroxyphenyl)imidazo[2,1-b]benzothiazole to the filtrate, the mixture was stirred for one hour at room temperature and then for 10 minutes at 50°–60° C. After cooling, insouble matters were filtered off and the filtrate was concentrated under reduced pressure. The residue was extracted with toluene and the extract was washed with 5% aqueous sodium hydrogen carbonate, dried over anhydrous magnesium sulfate, and then concentrated under reduced pressure to provide 8 g of 2-[m-(N-tert-butoxycarbonylglycyloxy)phenyl]imidazo[2,1-b]benzothiazole.

Melting point: 150° C.

(b) After heating 7 g of the product obtained in foregoing step (a) together with 140 ml of 1N hydrogen chloride ethanol solution for 15 minutes at 70°–80° C., the crystals thus precipitated were recovered by filtration, washed in succession with isopropanol and tetrahydrofuran, and dried to provide 5.5 g of 2-(m-glycyloxyphenyl)imidazo[2,1-b]benzothaizole dihydrochloride.

Melting point: above 190° C.
Elemental analysis for $C_{17}H_{17}N_3O_3SCl_2.H_2O$:

|  | C (%) | H (%) | N (%) | S (%) |
|---|---|---|---|---|
| Calculated: | 49.28 | 4.14 | 10.14 | 7.74 |
| Found: | 49.54 | 4.13 | 10.11 | 7.58 |

EXAMPLE 13

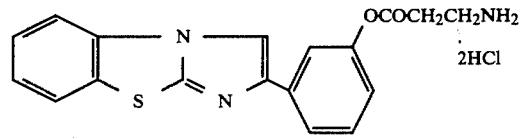

By following the same procedure as in Example 12 using 7.8 g of β-(N-tert-butoxycarbonyl)alanine and 2-(m-hydroxyphenyl)imidazo[2,1-b]benzothiazole, 5.2 g of m-(2-imidazo[2,1-b]benzothiazolyl)phenyl-3-aminopropionate dihydrochloride was obtained, through 2-[m-[β-(N-tert-butoxycarbonyl)alanyl]phenyl-]imidazo[2,1-b]benzothiazole (yield of 10.3 g, melting point of 184°–187° C.).

Melting point: above 160° C.
Elemental analysis for $C_{18}H_{17}N_3O_2SCl_2$:

|  | C (%) | H (%) | N (%) | S (%) |
|---|---|---|---|---|
| Calculated: | 52.69 | 4.18 | 10.24 | 7.81 |
| Found: | 52.99 | 4.26 | 10.12 | 7.94 |

EXAMPLE 14

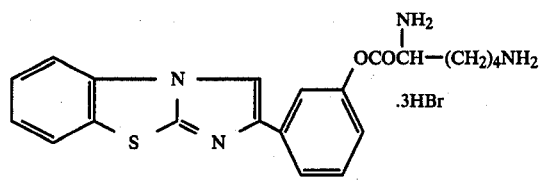

By following the same procedure as in Example 12 using 5 g of α-(N-tert-butoxycarbonyl)-ε-(N-carbobenzyloxy)lysine and 3 g of 2-(m-hydroxyphenyl)imidazo[2,1-b]benzothiazole to provide 5.5 g of 2-[m-(2-tert-butoxycarbonylamino-6-benzyloxycarbonylaminohexanoyloxy)phenyl]imidazo[2,1-b]benzothaizole (melting point of 162°–165° C.), the product was dissolved in 50 ml of 33% hydrogen bromide acetic acid solution and after stirring the solution for one hour at room temperature, the solution was concentrated under reduced pressure. The solids thus formed were washed with ether and dried to provide 5.2 g of 2-(m-lysyloxyphenyl)imidazo[2,1-b]benzothaizole trihydrobromide.

Melting point: 265°–267° C.
Elemental analysis for $C_{21}H_{25}N_4O_2SBr_3$:

|  | C (%) | H (%) | N (%) | S (%) | Br (%) |
|---|---|---|---|---|---|
| Calculated: | 39.58 | 3.95 | 8.79 | 5.03 | 37.62 |
| Found: | 39.31 | 3.96 | 8.81 | 5.00 | 37.49 |

EXAMPLE 15

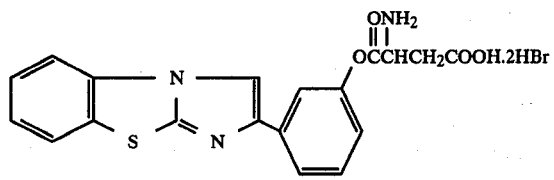

By following the same procedure as in Example 14 using 7 g of β-tert-butyl N-carbobenzyloxy-L-aspartate.dicyclohexylamine salt and 3.6 g of 2-(m-hydroxyphenyl)imidazo[2,1-b]benzothiazole, 5.7 g of 2-(m-α-aspartyloxyphenyl)imidazo[2,1-b]benzothiazole dihydrobromide hemi-hydrate was obtained through 2-[m-(3-tert-butoxycarbonyl-2-benzyloxycarbonylaminopropyionyloxy)phenyl]imidazo[2,1-b]benzothiazole (yield of 5.9 g).

Melting point: 170°–176° C.
Elemental analysis for $C_{38}H_{33}N_6O_9S_2Br_2$:

|  | C (%) | H (%) | N (%) | S (%) |
|---|---|---|---|---|
| Calculated: | 41.32 | 3.29 | 7.61 | 5.81 |
| Found: | 41.15 | 3.27 | 7.53 | 5.95 |

EXAMPLE 16

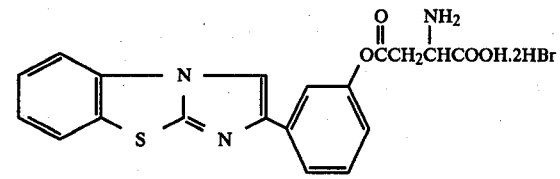

By following the same procedure as in Example 14 using 6.0 g of α-tert-butyl N-carbobenzyloxy-L-aspartate and 4.8 g of 2-(m-hydroxyphenyl)imidazo[2,1-b]benzothiazole, 5.1 g of 2-[m-(3-amino-3-carboxypropionyl)phenyl]imidazo[2,1-b]benzothiazole dihydrobromide was obtained through 2-[m-(3-tert-butoxycarbonyl-3-benzyloxycarbonylaminopropionyloxy)phenyl-]imidazo[2,1-b]benzothiazole (yield of 5.0 g).

Melting point: 195°–203° C.
Elemental analysis for $C_{19}H_{17}N_3O_4SBr_2$:

|  | C (%) | H (%) | N (%) | S (%) |
|---|---|---|---|---|
| Calculated: | 42.01 | 3.15 | 7.74 | 5.90 |
| Found: | 42.31 | 3.22 | 8.02 | 5.97 |

EXAMPLE 17

After cooling a mixed solution of 21 ml of phosphorus oxychloride and 200 ml of pyridine to −30° C., 10 g of 2-(m-hydroxyphenyl)imidazo[2,1-b]benzothiazole in 50 ml of pyridine was added gradually to the solution and the mixture was stirred for one hour at −30° C. The reaction mixture was poured into diluted hydrochloric acid-ice, crystals thus formed were recovered by filtration, washed in succession with water and ethanol, and dissolved in a diluted aqueous ammonia solution. After successively washing the solution with ether, ethyl acetate, and then toluene, insoluble matters thus formed were filtered off and the filtrate was concentrated under reduced pressure to about 100 ml. To the residue was added 200 ml of ethanol and after allowing to stand the mixture overnight in an ice-chamber, ammonium salts precipitated were recovered by filtration, and the ammonium salts were added to a mixture of concentrated hydrochloric acid and ice, then the mixture was stirred for 1 hour. The crystals precipitated were collected by filtration and washed with water, isopropanol and n-hexanane successively to provide 5.8 g of m-(imidazo[2,1-b]benzothiazol-2-yl)phenyl dihydrogenphosphate.

Melting point: 205°–208° C.
Elemental analysis for $C_{15}H_{11}N_2O_4PS.1/2H_2O$:

|  | C (%) | H (%) | N (%) |
|---|---|---|---|
| Calculated: | 50.71 | 3.40 | 7.88 |
| Found: | 50.73 | 3.21 | 8.05 |

EXAMPLE 18

By following the same procedure as in Example 2 using 0.34 g of 6-hydroxy-2-(p-methoxyphenyl)imidazo[2,1-b]benzothiazole and 0.3 g of malonic acid mono-p-methoxybenzyl ester, 0.3 g of 6-carboxyacetoxy-2-(p-methoxyphenyl)imidazo[2,1-b]benzothiazole hydrochloride was obtained through 2-(p-methoxyphenyl)-6-(p-methoxybenzyloxycarbonylacetoxy)imidazo[2,1-b]benzothiazole (yield of 0.4 g, melting point of 158°–160° C.).

Melting point: 169°–170° C.

Elemental analysis for $C_{19}H_{15}N_2O_5SCl$:

|  | C (%) | H (%) | N (%) | S (%) | Cl (%) |
|---|---|---|---|---|---|
| Calculated: | 54.48 | 3.61 | 6.69 | 7.65 | 8.46 |
| Found: | 54.52 | 3.70 | 6.59 | 7.70 | 8.53 |

EXAMPLE 19

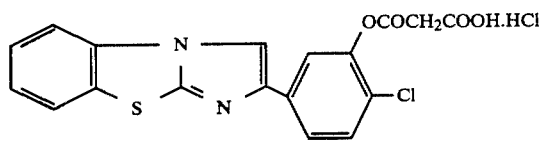

By following the same procedure as in Example 2 using 1.9 g of 2-(4-chloro-3-hydroxyphenyl)imidazo[2,1-b]benzothiazole and 2.7 g of malonic acid mono-p-methoxybenzyl ester, 1.05 g of 2-(3-carboxyacetoxy-4-chloro)phenylimidazo[2,1-b]benzothiazole.hydrochloride was obtained through 2-[3-(p-methoxybenzyloxycarbonylacetoxy)-4-chlorophenyl]imidazo[2,1-b]benzothiazole (yield of 1.45 g, melting point of 113°–115° C.).

Melting point: 157°–159° C.

Elemental analysis for $C_{18}H_{12}N_2O_4SCl_2$:

|  | C (%) | H (%) | N (%) | S (%) | Cl (%) |
|---|---|---|---|---|---|
| Calculated: | 51.08 | 2.86 | 6.62 | 7.57 | 16.75 |
| Found: | 51.28 | 2.67 | 6.59 | 7.56 | 16.50 |

EXAMPLE 20

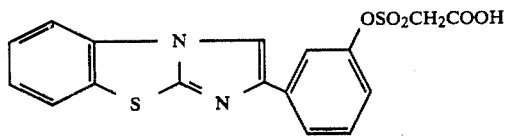

(a) In 80 ml of anhdyrous pyridine was dissolved 15 g of 2-(m-hydroxyphenyl)imidazo[2,1-b]benzothiazole and the solution was cooled and stirred at −20° to −25° C. To the solution was added dropwise a mixture of 20 ml of anhydrous dichloromethane and 5 g of chlorosulfonylacetyl chloride over a period of about 20 minutes and then the temperature of the solution was allowed to increase to room temperature. After 3 hours, the solvent was concentrated under reduced pressure, the residue was dissolved in 300 ml of chloroform, and the solution was washed in succession with diluted hydrochloric acid and then water, dried over anhydrous magneium sulfate, and concentrated to about 30 ml. To the residue was added hydrogen chloride ethanol solution to adjust the pH to 1–2 and crystals thus precipitated were recovered by filtration to provide 9.9 g of 2-[m-[m-(2-imidazo[2,1-b]benzothiazolyl)phenoxycarbonylmethylsulfonyloxy]phenyl]imidazo[2,1-b]benzothiazole dihydrochloride.

Melting point: 140°–143° C.

Elemental analysis for $C_{32}H_{22}N_4O_5S_3Cl_2$:

|  | C (%) | H (%) | N (%) | S (%) | Cl (%) |
|---|---|---|---|---|---|
| Calculated: | 54.16 | 3.13 | 7.90 | 13.55 | 9.99 |
| Found: | 54.25 | 3.26 | 7.80 | 13.59 | 9.65 |

(b) To a mixture of 150 ml of tetrahydrofuran, 100 ml of water, and 7.8 g of the product obtained in foregoing step (a) was added dropwise 33 ml of 1N aqueous potassium hydroxide solution under 10° C. over a period of 10 minutes, and then the mixture was stirred for 3.5 hours at room temperature. The reaction mixture thus obtained was washed thrice each time with 300 ml of ethyl acetate. The aqueous layer formed was adjusted to pH 1–2 by the addition of diluted sulfuric acid and the precipitates thus deposited were recovered by filtration to provide 2.5 g of 2-(m-carboxymethylsulfonyloxyphenyl)imidazo[2,1-b]benzothiazole.

Melting point: 156°–158° C.

Elemental analysis for $C_{17}H_{12}N_2O_5S_2$:

|  | C (%) | H (%) | N (%) | S (%) |
|---|---|---|---|---|
| Calculated: | 52.57 | 3.11 | 7.21 | 16.40 |
| Found: | 52.55 | 3.05 | 7.25 | 16.51 |

EXAMPLE 21

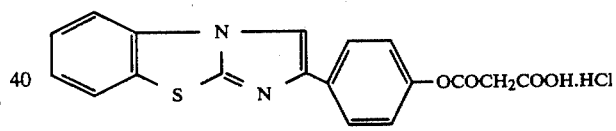

By following the same procedure as in Example 2 using 2.7 g of 2-(p-hydroxyphenyl)imidazo[2,1-b]benzothiazole and 2.7 g of malonic acid mono-p-methoxybenzyl ester, 2.2 g of 2-(p-carboxyacetoxyphenyl)imidazo[2,1-b]benzothiazole hydrochloride was obtained through 2-[p-(p-methoxyphenylmethoxycarbonylacetoxy)phenyl]imidazo[2,1-b]benzothiazole (yield of 3 g, melting point of 117°–119° C.).

Melting point: 193°–195° C.

Elemental analysis for $C_{18}H_{13}N_2O_4SCl$:

|  | C (%) | H (%) | N (%) | S (%) |
|---|---|---|---|---|
| Calculated: | 55.60 | 3.37 | 7.20 | 8.25 |
| Found: | 55.82 | 3.38 | 7.09 | 8.42 |

EXAMPLE 22

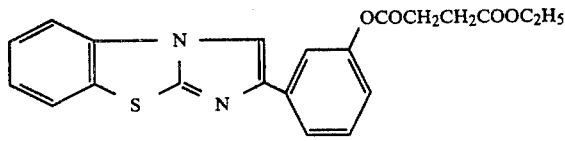

To a solution of 10 g of 2-(m-hydroxyphenyl)imidazo[2,1-b]benzothiazole and 9 g of succinic acid monoethyl ester dissolved in 100 ml of pyridine was added a solution of 11 g of dicyclohexylcarbodiimide dissolved in 10 ml of pyridine with stirring at 15°–25° C. and then the mixture was stirred for 3 hours at 20°–25° C. Urea thus precipitated was filtered off and the filtrate was concentrated under reduced pressure. The residue thus formed was dissolved in 100 ml of toluene and the solution was washed twice each time with 100 ml of water, dried over anhydrous magnesium sulfate, and the solvent was distilled off under reduced pressure. The sticky residue thus formed was applied to silica gel column chromatography and the product was eluted with a mixture of benzene and ethyl acetate (9:1 by volume ratio) to provide 8.9 g of 2-[m-(3-ethoxycarbonylpropionyloxy)phenyl]imidazo[2,1-b]benzothiazole.

Melting point: 70°–74° C. (hydrochloride: 155°–159° C.).

Elemental analysis for $C_{21}H_{18}N_2O_4S$:

| | C (%) | H (%) | N (%) | S (%) |
|---|---|---|---|---|
| Calculated: | 63.95 | 4.60 | 7.10 | 8.13 |
| Found: | 64.03 | 4.43 | 7.16 | 8.11 |

EXAMPLE 23

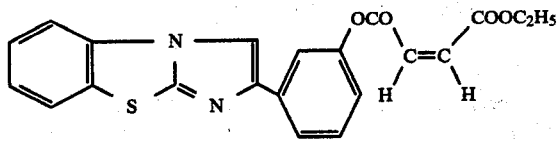

By following the same procedure as in Example 22 using 3.2 g of 2-(m-hydroxyphenyl)imidazo[2,1-b]benzothiazole and 3.2 g of adipic acid monoethyl ester, 1.8 g of 2-[m-(5-ethoxycarbonylpentanoyloxy)phenyl]imidazo[2,1-b]benzothiazole was obtained.

Melting point: 90°–92° C.

Elemental analysis for $C_{23}H_{22}N_2O_4S$:

| | C (%) | H (%) | N (%) | S (%) |
|---|---|---|---|---|
| Calculated: | 65.39 | 5.25 | 6.63 | 7.59 |
| Found: | 65.57 | 5.32 | 6.72 | 7.41 |

EXAMPLE 24

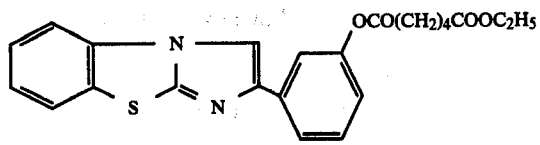

By following the same procedure as in Example 22 using 10 g of 2-(m-hydroxyphenyl)imidazo[2,1-b]benzothaizole and 8.3 g of malic acid monoethyl ester, 7.2 g of 2-[m-(cis-3-ethoxycarbonylpropenoyloxy)phenyl]imidazo[2,1-b]benzothiazole was obtained.

Melting point: 126°–128° C.

Elemental analysis for $C_{21}H_{16}N_2O_4S$:

| | C (%) | H (%) | N (%) | S (%) |
|---|---|---|---|---|
| Calculated: | 64.27 | 4.11 | 7.14 | 8.17 |
| Found: | 64.34 | 3.81 | 7.23 | 7.99 |

EXAMPLE 25

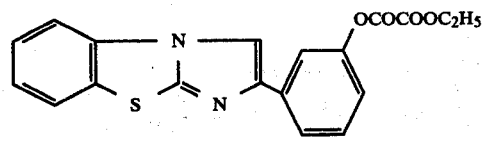

To a mixture of 4 g of 2-(m-hydroxyphenyl)imidazo[2,1-b]benzothiazole, 1.52 g of triethylamine, and 50 ml of tetrahydrofuran was added a mixture of 2.1 g of ethyl oxalyl chloride and 10 ml of tetrahydrofuran at a temperature below −10° C. Thereafter, the reaction mixture was stirred overnight at room temperature and then concentrated under reduced pressure. The residue thus formed was dissolved in 200 ml of toluene. The toluene solution was washed with water, dried over anhydrous magnesium sulfate, and concentrated under reduced pressure. The residue was applied to silica gel column chromatography (80 ml of silica gel, eluate: a mixture of toluene and ethyl acetate (9:1)) to provide 2.75 g of 2-(m-ethoxalyloxyphenyl)imidazo[2,1-b]benzothiazole.

Melting point: 120°–121° C.

Elemental analysis for $C_{19}H_{14}N_2O_4S$:

| | C (%) | H (%) | N (%) | S (%) |
|---|---|---|---|---|
| Calculated: | 62.29 | 3.85 | 7.65 | 8.75 |
| Found: | 62.48 | 3.76 | 7.50 | 8.74 |

EXAMPLE 26

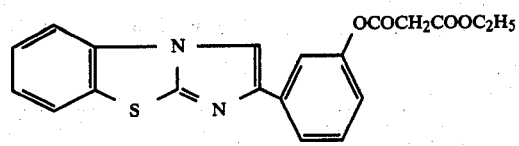

To a mixture of 4 g of 2-(m-carboxyacetoxyphenyl)imidazo[2,1-b]benzothiazole, 0.52 g of ethanol, and 50 ml of tetrahydrofuran was added a mixture of 2.3 g of dicyclohexylcarbodiimide and 10 ml of tetrahydrofuran at a temperature below 10° C. Thereafter, the mixture was stirred overnight at room temperature. Dicyclohexyl urea thus formed was filtered off and the filtrate was concentrated under reduced pressure. The residue was applied to silica gel column chromatography (80 ml of silica gel, eluate: a mixture of toluene and ethyl acetate (9:1)) to provide 2.0 g of oily 2-(m-ethoxycarbonylacetoxyphenyl)imidazo[2,1-b]benzothiazole.

Nuclear magnetic resonance spectra (CDCl₃):

δ (ppm): 1.33 (t, 3H, —CH₂CH₃)
3.61 (s, 2H, —COCH₂CO—)
4.28 (q, 2H, —CH₂CH₃)

7.93 (s, 1H, 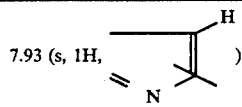 )

EXAMPLE 27

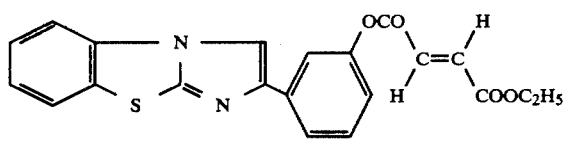

By following the same procedure as in Example 22 using 11.5 g of 2-(m-hydroxyphenyl)imidazo[2,1-b]benzothaizole and 9.2 g of fumaric acid monoethyl ester. 7.3 g of 2-[m-(trans-3-ethoxycarbonylpropenoyloxy)-phenyl]imidazo[2,1-b]benzothiazole was obtained.

Melting point: 130°–130.5° C.

Elemental analysis for $C_{21}H_{16}N_2O_4S$:

|  | C (%) | H (%) | N (%) | S (%) |
| --- | --- | --- | --- | --- |
| Calculated: | 64.27 | 4.11 | 7.14 | 8.17 |
| Found: | 64.38 | 3.95 | 7.19 | 8.21 |

EXAMPLE 28

(1) Preparation of tablet of 100 mg in weight.

| Compound of Example 2b | 5 mg |
| --- | --- |
| Crystal cellulose | 30 mg |
| Crystal milk sugar | 64 mg |
| Magnesium stearate | 1 mg |

The foregoing components were sufficiently mixed and formed into tablets using a punch of 6.5 mm in diameter.

(2) Preparation of capsule having inside weight of 180 mg:

| Compound of Example 2b | 5 mg |
| --- | --- |
| Crystal milk sugar | 119 mg |
| Corn starch | 54 mg |
| Magnesium stearate | 2 mg |

The foregoing components were sufficiently mixed and were filled in a #4 hard capsule.

(3) Preparation of injection:

To about 100 ml of distilled water for injection were added 1 g of the compound obtained in Example 2b and 0.5 g or L-alginine and the mixture was sufficiently mixed to dissolve the components and then distilled water for injection was further added thereto to make the total volume to 250 ml. After filtering the solution using a membrane filter having pore size of 0.22 μm, 0.5 ml each of the solution was placed in a vial and after lyophilizing the solution, the vial was sealed by a rubber stopper.

What is claimed is:

1. A 2-phenylimidazo(2,1-b)benzothiazole compound represented by general formula I:

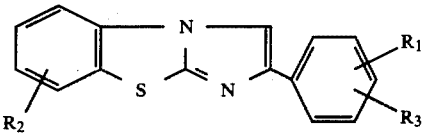

wherein $R_1$ represents a group shown by the formula —O—A—$(B)_n$—D (wherein A represents a carbonyl group or a sulfonyl group; B represents a saturated or unsaturated lower alkylene group which may be substituted by a carboxy group, an amino group, or a lower alkoxy group and may be interrupted by an oxygen atom; n represents 0 or 1; and D represents a carboxy group, a lower alkoxycarbonyl group, an amino group, or a mono- or di-lower alkylamino group) or a phosphoric acid residue

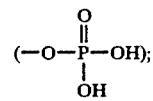

and $R_2$ represents a hydrogen atom or a carboxyacetoxy group, with the proviso that $R_1$ is a hydrogen atom when $R_2$ is a carboxyacetoxy group; and $R_3$ represents a hydrogen atom, a halogen atom, or a lower alkoxy group and the salts thereof.

2. The compound as claimed in claim 1 wherein the compound is represented by general formula I':

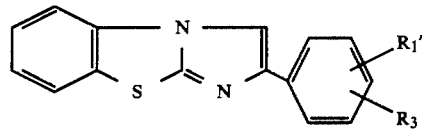

wherein $R'_1$ represents a group shown by the formula —O—CO—B—D' (wherein B has the same significance as in general formula I in claim 1 and D' represents a carboxy group, an amino group, or a mono- or di-lower alkyl-amino group) and $R_3$ represents a hydrogen atom, a chlorine atom, or a methoxy group and the salts thereof.

3. The compound as claimed in claim 1 wherein the compound is represented by general formula I''

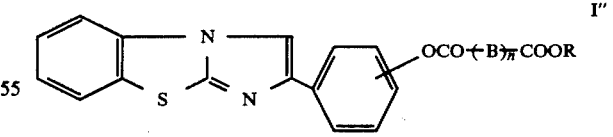

wherein B and n have the same significance as in general formula I and R represents a hydrogen atom or a lower alkyl group and the salts thereof.

4. The compound as claimed in claim 1 wherein the compound is 2-(m-carboxyacetoxyphenyl)imidazo[2,1-b]benzothiazole and the salts thereof.

5. The compound as claimed in claim 1 wherein the compound is 2-(m-trans-3-carboxypropenoyloxyphenyl)imidazo[2,1-b]benzothiazole and the salts thereof.

6. The compound as claimed in claim 1 wherein the compound is 2-(m-cis-3-carboxypropenoyloxyphenyl)imidazo[2,1-b]benzothiazole and the salts thereof.

7. The compound as claimed in claim 1 wherein the compound is 2- m-(3-ethoxycarbonylpropionyloxy)phenyl imidazo[2,1-b]benzothiazole and the salts thereof.

8. The compound as claimed in claim 1 wherein the compound is 2-[m-(trans-3-ethoxycarbonylpropenoyloxy)phenyl]imidazo[2,1-b]benzothiazole and the salts thereof.

9. A composition for suppressing a delayed type hypersensitivity reaction containing an effective amount of the compound or the salt thereof as claimed in claim 1.

* * * * *